(12) United States Patent
Brown

(10) Patent No.: US 8,731,257 B2
(45) Date of Patent: May 20, 2014

(54) ANALYSIS OF RADIOGRAPHIC IMAGES

(75) Inventor: Kevin Brown, West Sussex (GB)

(73) Assignee: Elekta AB (Publ), Stockholm (SE)

( * ) Notice: Subject to any disclaimer, the term of this patent is extended or adjusted under 35 U.S.C. 154(b) by 269 days.

(21) Appl. No.: 13/132,805

(22) PCT Filed: Dec. 8, 2008

(86) PCT No.: PCT/EP2008/010396
§ 371 (c)(1),
(2), (4) Date: Jun. 3, 2011

(87) PCT Pub. No.: WO2010/066265
PCT Pub. Date: Jun. 17, 2010

(65) Prior Publication Data
US 2011/0243387 A1    Oct. 6, 2011

(51) Int. Cl.
*G06K 9/00*   (2006.01)

(52) U.S. Cl.
USPC .......................................................... 382/128

(58) Field of Classification Search
None
See application file for complete search history.

(56) References Cited

U.S. PATENT DOCUMENTS

| | | | |
|---|---|---|---|
| 7,356,112 B2 * | 4/2008 | Brown et al. | 378/8 |
| 7,869,562 B2 * | 1/2011 | Khamene et al. | 378/20 |
| 2008/0031404 A1 * | 2/2008 | Khamene et al. | 378/6 |
| 2008/0144772 A1 * | 6/2008 | Yi et al. | 378/65 |

(Continued)

FOREIGN PATENT DOCUMENTS

CN    101238391    8/2008

OTHER PUBLICATIONS

S S. Vedam, P J Keall, V R Kini, HMostafavi, H P Shukla and R Mohan, "Acquiring a four-dimensional computed tomography dataset using an external respiratory signal" Phys. In Medicine and Biology, 4B. 2003.*
International Search Report, Jul. 27, 2009.

(Continued)

*Primary Examiner* — Barry Drennan
*Assistant Examiner* — Oneal R Mistry
(74) *Attorney, Agent, or Firm* — Westman, Champlin & Koehler, P.A.; Z. Peter Sawicki; Amanda Prose

(57) ABSTRACT

The present invention therefore provides a method for the analysis of radiographic images, comprising the steps of acquiring a plurality of projection images of a patient, acquiring a surrogate signal indicative of the location of a target structure in the patient, reconstructing a plurality of volumetric images of the patient from the projection images, each volumetric image being reconstructed from projection images having a like breathing phase, identifying the position of the target structure such as a tumor in each volumetric image, associating a surrogate signal with each of the projection images, and determining a relationship between the surrogate signal and the position of the target structure. Multiple projection images having a like breathing phase can be grouped for reconstruction, to provide sufficient numbers for reconstruction. The analysis of the multiple values of the surrogate associated with each breathing phase can be used to determine the mean surrogate value and its variation. Multiple values of the surrogate signal associated with the same nominal breathing phase can be used to determine a mean value of the surrogate signal for the target position associated with that phase and a variation of the value of the surrogate signal for the target position associated with that phase. The breathing phase of specific projection images can be obtained by analysis of one or more features in the images, such as the method we described in U.S. Pat. No. 7,356,112, or otherwise.

7 Claims, 4 Drawing Sheets

(56) References Cited

U.S. PATENT DOCUMENTS

| | | | |
|---|---|---|---|
| 2008/0177280 A1* | 7/2008 | Adler et al. | 606/130 |
| 2008/0212737 A1* | 9/2008 | D'Souza et al. | 378/65 |
| 2008/0253636 A1* | 10/2008 | Deller | 382/131 |
| 2012/0004518 A1* | 1/2012 | D'Souza et al. | 600/301 |

OTHER PUBLICATIONS

Written Opinion, Jul. 27, 2009.

Chinese Office Action; 200880132282.3; Dec. 12, 2012.

* cited by examiner

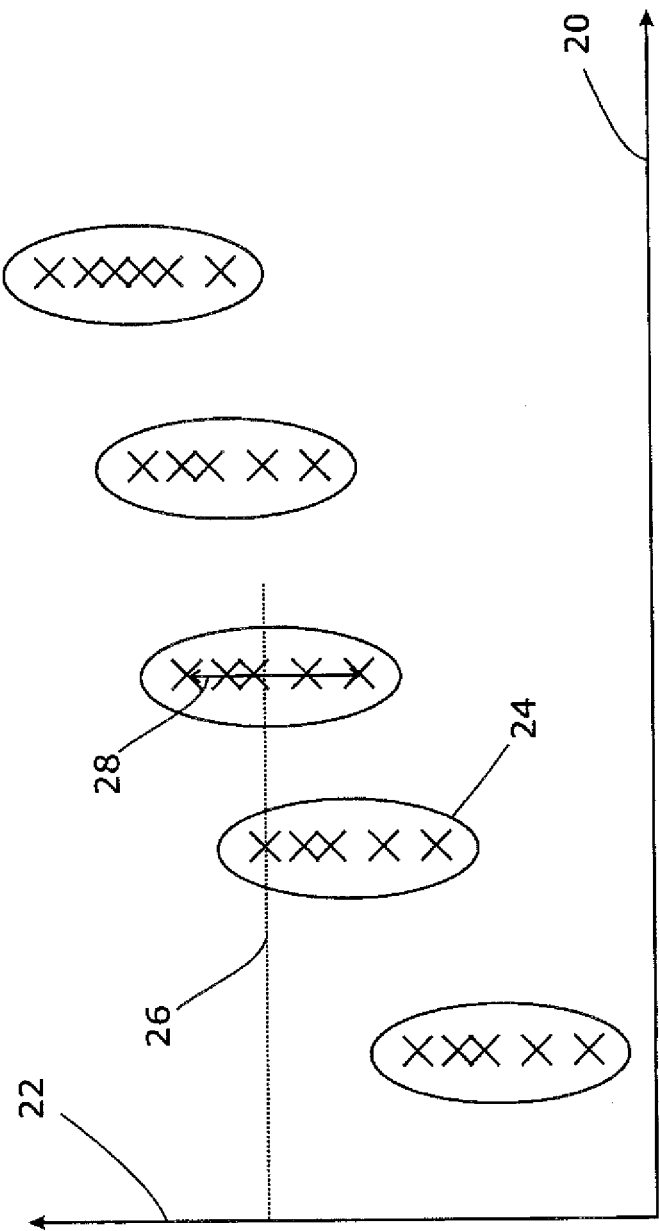

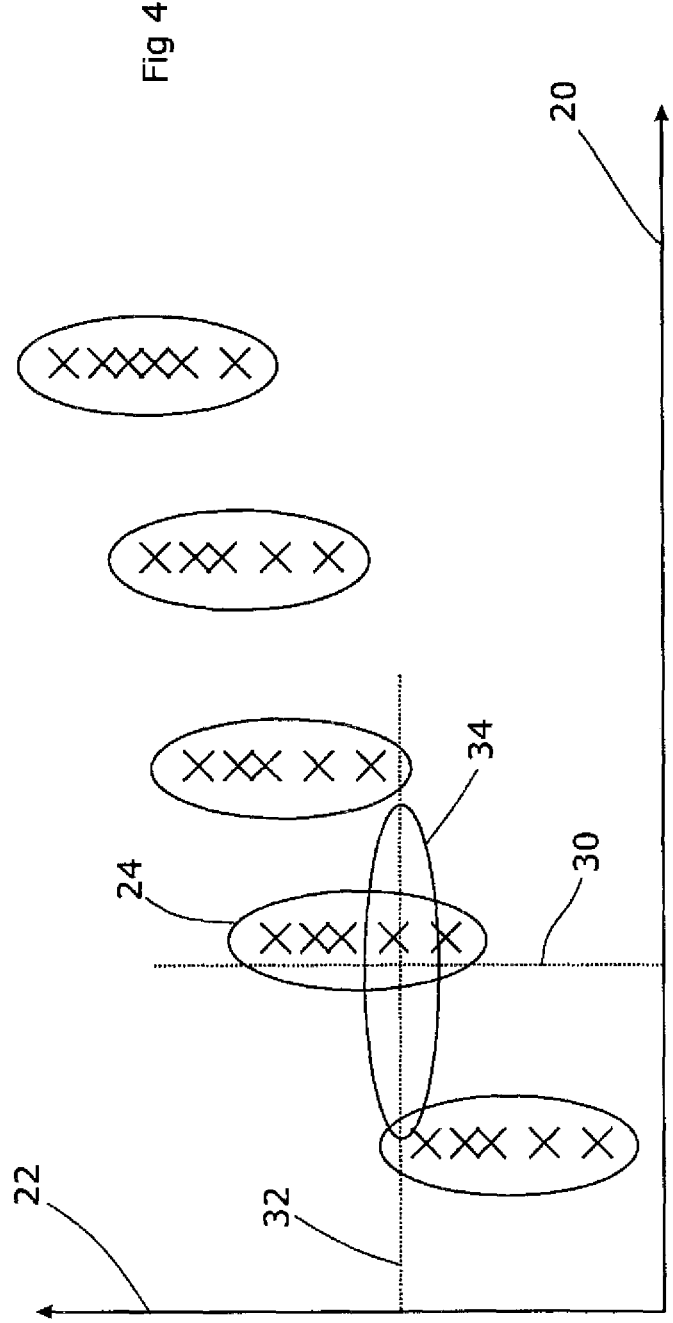

ANALYSIS OF RADIOGRAPHIC IMAGES

CROSS-REFERENCE TO RELATED APPLICATION

This Application is a Section 371 National Stage Application of International Application No. PCT/EP2008/010396, filed Dec. 8, 2008 and published as WO 2010/066265 A1 on Jun. 17, 2010, the content of which is hereby incorporated by reference in its entirety.

FIELD OF THE INVENTION

The present invention relates to the analysis of radiographic images.

BACKGROUND ART

Radiotherapeutic apparatus and techniques have now developed to the point where it is likely that some form of tracking or gating system to reduce the effects of tumour motion (primarily due to breathing) will soon be feasible. Such techniques offer significant advantages in terms of the treatment of tumours in the chest and lung area. They require, however, a source of information as to the current location of the tumour, during treatment, in real time. As yet, this is not available, a factor which has the potential to delay their introduction.

Most existing respiration correlation systems use some form of surrogate monitoring system which has a fast response time, in conjunction with a correlation to the internal tumour position. In other words, rather than try to achieve the difficult task of monitoring the actual position of the tumour, either a feature in the patient is identified, or a marker is provided, whose position can more easily be tracked and is correlated with that of the tumour.

Current surrogate monitoring systems include the Varian RPM system, in which an external marker on the surface of the patient is monitored by a camera, the VisionRT camera-based surface tracking system, the Accuray system using a marker vest and cameras, and our use of a pressure sensor in the abdominal compression plate (see WO2008/040379).

Various problems exist with certain of these systems. One problem is how representative these surrogate monitoring systems are of the internal tumour position. For example, some systems generate a correlation between the position of the external marker and the internal tumour position on the 4D planning CT. Some studies show that this correlation is not stable and therefore not valid after a period of time. The use of 4D CT is useful in that it allows the visualisation of soft tissue target and critical structures, but it can not be easily repeated to ensure the correlation continues to be valid. Additionally, 4D CT generally only uses a few breathing cycles per slice, which gives a low statistical confidence in the result.

The Accuray system uses oblique kV planar imaging systems to generate the correlation between marker vest and internal tumour position. The system then periodically checks the correlation and repeats this as required. The change in correlation is particularly a problem for this technique due to the extended treatment time. The use of kV planar imaging systems is good in that it can be easily repeated, but it does not easily allow the visualisation of soft tissue target and critical structures. This system also tends to use very few breathing cycles to determine the correlation, which gives a low statistical confidence in the result.

SUMMARY OF THE INVENTION

The present invention therefore provides a method of determining the relationship between a target position and surrogate signal, comprising the steps of acquiring a plurality of projection images of a patient, acquiring a surrogate signal indicative of the location of a target structure in the patient, reconstructing a plurality of volumetric images of the patient from the projection images, each volumetric image being reconstructed from projection images having a like breathing phase, identifying the position of the target structure in each volumetric image, associating a surrogate signal for the target motion with each projection image, determining a relationship between surrogate signal and the position of the target structure.

Such a method allows a surrogate signal, such as (but not limited to) those mentioned above, to be quickly calibrated to the internal position of a target such as tumour so that the surrogate signal can be reliably and confidently used during treatment.

The breathing phase of specific projection images can be obtained by analysis of one or more features in the images, such as the method we described in U.S. Pat. No. 7,356,112, or otherwise.

Projection images having a like breathing phase can be grouped for reconstruction, to provide sufficient numbers for reconstruction. This will mean that there will be some variation in the exact breathing phase of images in the same group, but the use of a sufficient number of images and the statistical methods applied to the results mean that the method can be resilient to this.

Generally, the allocation of projection images into groups having like breathing phases means that there will be multiple values of the surrogate signal (associated with corresponding multiple projection images), all associated with the same nominal breathing phase. These can be used to determine a mean value of the surrogate signal for the target position associated with that phase. Similarly, the multiple values of the surrogate signal associated with a particular nominal breathing phase can be used to determine a variation of the value of the surrogate signal for the target position associated with that phase. This allows a confidence level to be associated with the correlation between particular surrogate signals and particular target positions.

The surrogate signal will usually be one having a low latency, to allow it to be used for gating the radiation beam or tracking the target position.

BRIEF DESCRIPTION OF THE DRAWINGS

An embodiment of the present invention will now be described by way of example, with reference to the accompanying figures in which;

FIGS. 3 and 4 show the derivation of tumour position and confidence data from the correlation.

DETAILED DESCRIPTION OF THE EMBODIMENTS

The invention seeks to establish a relationship between a surrogate signal and the actual tumour position that is stable over a sufficient period of time to allow for treatment, so that the tumour location can be reliably and swiftly determined prior to and during treatment and the surrogate signal can be used to drive a tracking or gating system.

Figure 1:
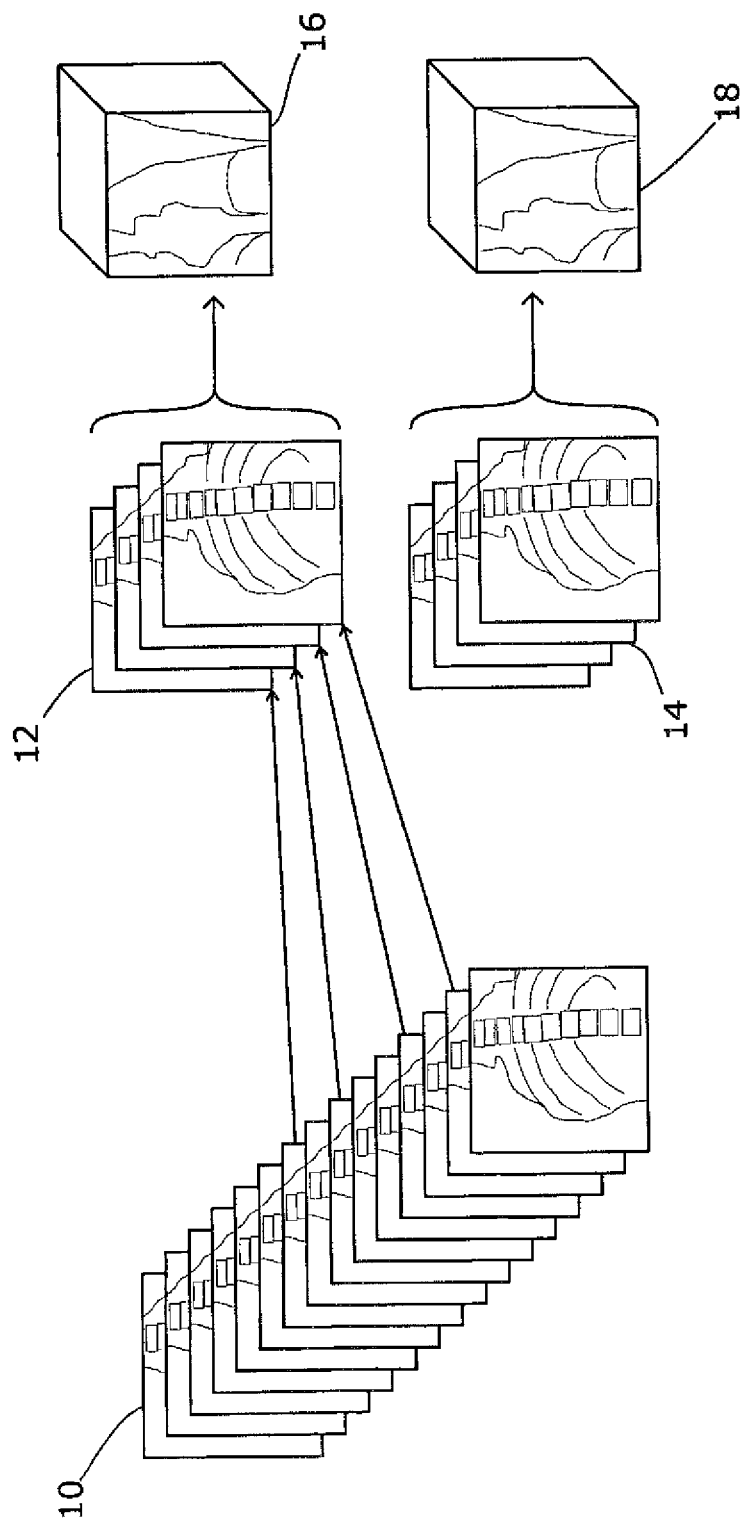
FIG. 1 shows a process for creating a 4D CT dataset.

Prior to treatment, a CT scan of the region of interest is taken. As shown in FIG. 1, this involves acquiring a series of projection images 10, i.e. a plurality of 2D x-ray images of the region taken from a range of different directions as the imaging head rotates around the patient. Typically, this rotation is about the cranio-cordal axis of the patient.

As each image is acquired, the value of the surrogate signal to be calibrated is recorded and stored in a manner associated with the image. Each image is then assigned a breathing phase; our preferred way of doing so at present is to analyse the features in the image as set out in our earlier patent U.S. Pat. No. 7,356,112; that document is therefore incorporated herein by reference and readers are alerted that a reading of that document is essential to a thorough understanding of the present invention. A feature in the image such as the position of the diaphragm provides a suitable indicator of breathing phase. Other features in the image or other methods of determining breathing phase can be employed, however. Once each image has been allocated a phase, they can be allocated to a suitable group of images 12, 14 consisting of images with like (i.e. similar) phase. Separate CT reconstructions 16, 18 are then obtained from each group 12, 14; each CT reconstruction therefore provides a high quality three-dimensional image of the patient structure at a specific point in the breathing cycle.

Figure 2:
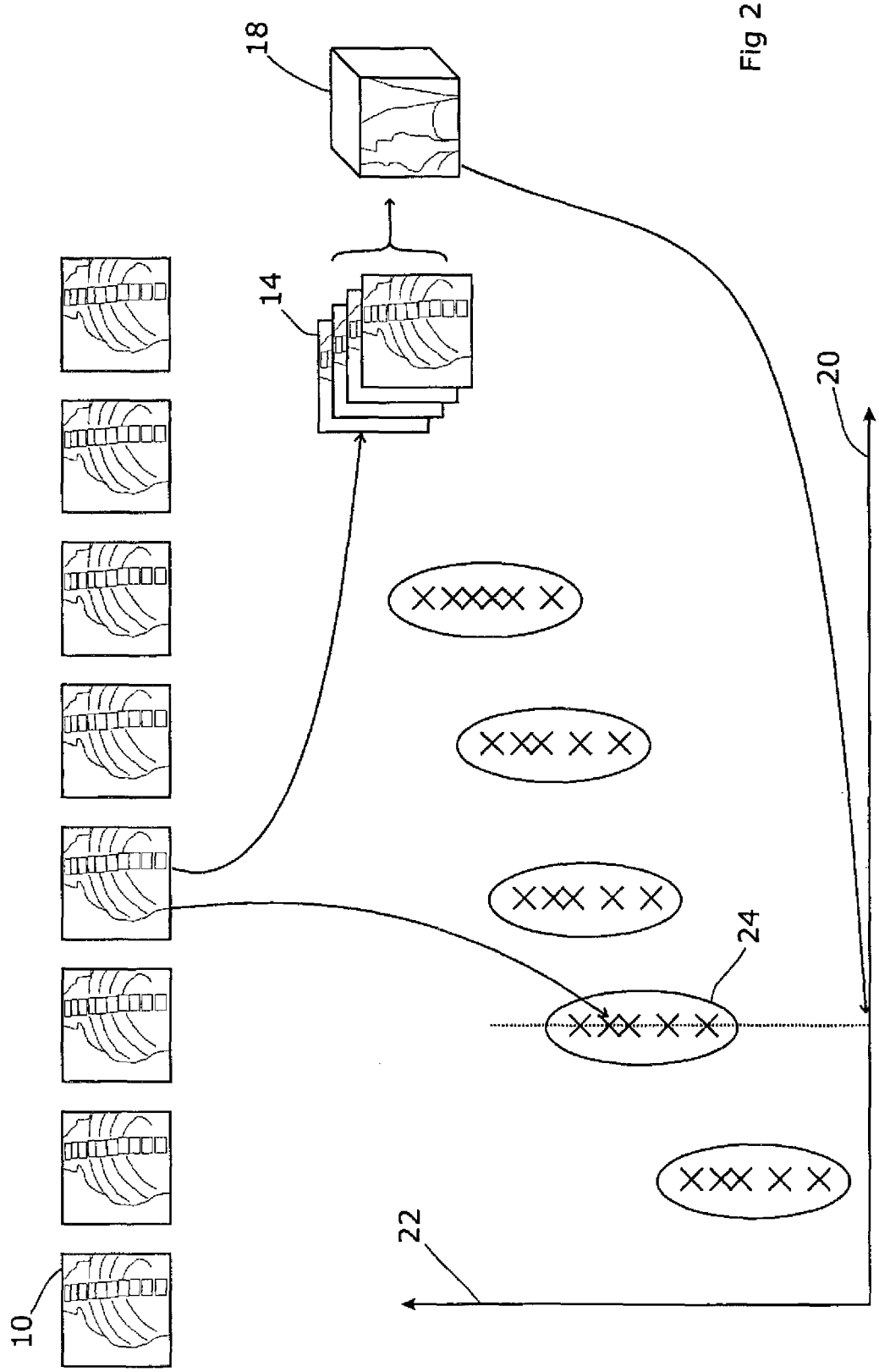
FIG. 2 shows a process for correlation of the surrogate signal and tumour positions.

After reconstruction is completed, the tumour position is determined in each reconstruction, i.e. in each breathing phase. This position can be identified manually by a clinician in each reconstruction, or having identified the position in one reconstruction the position in all other reconstructions can be determined by automated (or semi-automated) analysis of the reconstructions. The value of the surrogate associated with each of the images that contributed to each reconstruction is, of course, already known and recorded. This means that a relationship between the tumour position and the surrogate value can be plotted and analysed. FIG. 2 shows a graph of the relationship, in which the tumour position is plotted along the x axis 20 and the surrogate value plotted along the y axis 22. As can be seen, the process of grouping the images into like breathing phases means that points in the plot (corresponding to images) appear in vertical groups 24, i.e. having nominally the same breathing phase but different surrogate signal values. However, a relationship between surrogate value and breathing phase is clear.

To summarise, the surrogate value associated with each image 10 yields the y position of the plot point corresponding to that image. Images are also grouped according to their breathing phase, and each group 14 is reconstructed to yield a CT dataset 18 from which the tumour position and hence the x position is determined.

Thus, both the mean value 26 of the surrogate and its variation 28 can be calculated for each breathing phase, and hence for each of a certain number of tumour positions, as illustrated in FIG. 3. More usefully, as shown in FIG. 4, this data can be used to calculate the most likely position 30 of the tumour for any given value 32 of the surrogate. This most likely value 30 can be used to drive the tracking or gating system. Furthermore, as also shown in FIG. 4, the data can be used to derive a confidence value 34 associated with this most likely value 30, and this confidence value 34 indicates the likely residual error associated with the correlation. This can be used to determine the safety margins that are necessary to ensure that the tumour is satisfactorily irradiated.

Therefore the present invention creates a correlation that;
is based on many breathing cycles, so more representative of the actual correlation. More data gives more confidence in the most likely value.
contains a confidence calculation to inform the residual safety margins
can be used to determine the correlation to a soft tissue target which would not be visible on planar imaging
can be also used to determine the correlation not only to the target but also to critical structures which are not generally visible on planar imaging In order to visualise the motion, the images are acquired more slowly to image sufficient breathing cycles (typically about 60) for the reconstruction. This does not require any special effort by the user, as all the settings for the scan can be stored in the preset for that patient.

All of the above can, using modem computer hardware, happen simultaneously with the image acquisition process. The result of this is that at the end of the scan, the user can presented with a 4D volumetric image almost instantaneously.

It will of course be understood that many variations may be made to the above-described embodiment without departing from the scope of the present invention. Although the present invention has been described with reference to preferred embodiments, workers skilled in the art will recognize that changes may be made in form and detail without departing from the spirit and scope of the invention.

Although the present invention has been described with reference to preferred embodiments, workers skilled in the art will recognize that changes may be made in form and detail without departing from the spirit and scope of the invention.

The invention claimed is:

1. A method of determining the relationship between a target position and surrogate signal, comprising the steps of:
   acquiring a plurality of projection images of a patient;
   as each projection image is acquired, acquiring a surrogate signal indicative of the location of a target structure in the patient and associating values of the surrogate signal with each of the projection images;
   analysing the projection images for their breathing phase on the basis of a feature in the images;
   reconstructing a plurality of volumetric images of the patient from the projection images, each volumetric image being reconstructed from projection images having a like breathing phase;
   identifying the position of the target structure in each volumetric image; and
   determining a relationship between the surrogate signal and the position of the target structure.

2. The method according to claim 1 in which the target structure is a tumour.

3. The method according to claim 1 in which multiple values of the surrogate signal associated with multiple projection images having a like breathing phase are used to determine a mean value of the surrogate signal for the target position associated with that phase.

4. The method according to claim 1 in which multiple values of the surrogate signal associated with a breathing phase are used to determine a variation of the value of the surrogate signal for the target position associated with that phase.

5. The method according to claim 2 in which multiple values of the surrogate signal associated with multiple projection images having a like breathing phase are used to determine a mean value of the surrogate signal for the target position associated with that phase.

6. The method according to claim 2 in which multiple values of the surrogate signal associated with a breathing phase are used to determine a variation of the value of the surrogate signal for the target position associated with that phase.

7. The method according to claim 3 in which multiple values of the surrogate signal associated with a breathing phase are used to determine a variation of the value of the surrogate signal for the target position associated with that phase.

\* \* \* \* \*